United States Patent [19]

Kiechel et al.

[11] Patent Number: 4,885,305

[45] Date of Patent: Dec. 5, 1989

[54] NASAL COMPOSITIONS

[75] Inventors: Jean-René Kiechel, Rueil-Malmaison; Francoise Acezat-Mispelter, Elancourt; Danielle Plas, Rueil-Malmaison, all of France

[73] Assignee: Yamanouchi Pharmaceutical Co., Ltd., Tokyo, Japan

[21] Appl. No.: 294,902

[22] Filed: Jan. 5, 1989

Related U.S. Application Data

[63] Continuation of Ser. No. 127,817, Dec. 2, 1987, abandoned, which is a continuation of Ser. No. 764,866, Aug. 12, 1985, abandoned.

[30] Foreign Application Priority Data

Aug. 10, 1984 [FR] France .................................. 84 12668

[51] Int. Cl.$^4$ ............................................. A61K 31/44
[52] U.S. Cl. ...................................................... 514/356
[58] Field of Search ............................................. 514/356

[56] References Cited

U.S. PATENT DOCUMENTS

| | | | |
|---|---|---|---|
| 4,497,821 | 2/1985 | Wehinger et al. | 514/356 |
| 4,525,341 | 6/1985 | Deihl | 514/356 |
| 4,537,898 | 8/1985 | Hoff et al. | 514/941 |
| 4,607,041 | 8/1986 | Baxter et al. | 514/356 |
| 4,622,332 | 11/1986 | Wehinger et al. | 514/356 |
| 4,686,217 | 8/1987 | Baxter et al. | 514/318 |
| 4,722,931 | 2/1988 | Casanova et al. | 514/338 |

OTHER PUBLICATIONS

Dittert, Sprowls' American Pharmacy, 7th Ed. (1974) p. 416.
Letters to the Editor, J. Pharm. Pharmac., 1972, 24; 917; Loev et al.
European Journal of Pharmacology, 54 (1979) 289–293 Jolly et al.
Van De Donk et al; First European Congress of Biopharmaceutics and Pharmacokinetics; pp. 406–414.
Sucken et al; Pharmazeutische Technologie, Deutschland (1978), pp. 722–729; English Translation enclosed.

*Primary Examiner*—Allen J. Robinson
*Attorney, Agent, or Firm*—Burgess, Ryan & Wayne

[57] ABSTRACT

Novel nasal pharmaceutical composition adapted to be absorbed systemically through the nasal mucus and comprising as active agent a calcium antagonist selected from optionally substituted, 1,4-dihydropyridines bearing in the 4 position a monocyclic ring, together with a nontoxic pharmaceutically aceptable nasal carrier therefor.

10 Claims, No Drawings

NASAL COMPOSITIONS

This application is a continuation of application Ser. No. 127,817, filed 12/2/87, now abandoned, which is a continuation of U.S. Ser. No. 764,877, filed Aug. 12, 1985, now abandoned.

The present invention relates to novel dosage forms containing calcium antagonists, adapted for nasal administration.

Calcium antagonists, also called calcium channel blocking agents, represent a group of active agents which are useful as sole therapy for a variety of diseases inter alia against angina pectoris, hypertension, cerebral insufficiency and in certain cases against migraine. A particular class of calcium antagonists comprises optionally substituted 1,4-dihydropyridines bearing in the 4 position a monocyclic ring (hereinafter these compounds are referred to as calcium antagonists of the invention). The ring may be for example phenyl or pyridyl optionally substituted by at least one monovalent radical. Two well known calcium antagonists of the invention are nicardipine and nifedipine. Nifedipine has been administered as a pulmonary spray in order to determine its action on the lungs. Generally calcium antagonists are administered orally (including sublingually) or by injection in order to obtain a systemic effect. However, these drugs administered in such forms may have a short duration of action. Repeated oral or parenteral administration many times a day in order to maintain adequate blood levels of the drugs is an handicap for the patient. A serious need exists therefore for improved delivery systems for calcium antagonists of the invention. Up till now the calcium antagonists of the invention have not been administered systemically by nasal route for therapy of diseases.

According to the present invention, it has been surprisingly found that calcium antagonists selected from the class of optionally substituted 1,4-dihydropyridines bearing in the 4 position a monocyclic ring can be administered nasally with results superior to those obtained by oral administration. The nasal administration of the calcium antagonists of the invention is a particularly suitable mode of administration, especially when high blood levels of drug are required immediately after administration, e.g. for the treatment of acute attacks of angina pectoris, hypertension, etc. . . . In one aspect the invention provides a nasal pharmaceutical composition adapted to be absorbed systemically through the nasal mucus and comprising as active agent a calcium antagonist selected from optionally substituted 1,4-dihydropyridines bearing in the 4 position a monocyclic ring, together with a nontoxic pharmaceutically acceptable nasal carrier therefor. In another aspect the invention provides the use of an optionally substituted 1,4-dihydropyridine bearing in the 4 position a monocyclic ring in the manufacture of a composition for systemic administration to as a nasal composition.

Especially preferred calcium antagonists include 1,4-dihydro-4-phenylpyridines such as Bay k 9320, felodipine, fluordipine, FR 7534, FR 34 235, FR 38 245, mesudipine, nicardipine, nifedipine, niludipine, nimodipine, nisoldipine, nitrendipine and SKF 24 260. Such calcium antagonists are known and are described in the art.

Most preferred calcium antagonists are those which are water-soluble including nicardipine.

The nasal pharmaceutical compositions of the present invention may be in conventional form for systemic administration of the active agent through the nasal mucus membranes, using conventional nasal applicators. Such pharmaceutical compositions and applicators may be produced in conventional manner (see for example Remington's Pharmaceutical Sciences, 16th Edition, edited by A. Osol, Mack, Pennsylvania, particularly pages 1614-1628 and Pharmazeutische Technologie, edited by H. Sucker and Co., Georg Thieme Verlag, Germany, 1978, p. 722-729).

The nasal pharmaceutical compositions of the invention may be in solid form or preferably in liquid form. The compositions must be formulated in order to provide an effective amount of active agent per dose, to be sufficiently stable and compatible with the nasal mucus and to have for example a well-tolerated osmolarity and pH.

When the nasal pharmaceutical compositions of the invention are in liquid form, a solvent such as water may be used. A co-solvent such as propylene glycol may be present, preferably in a concentration of less than 10% e.g. 0.1 to 10%. The composition is preferably in the form of an aqueous solution. Alernatively it may be in the form of a suspension or an emulsion.

If desired, the nasal pharmaceutical compositions of the invention may be in powder form. Preferably the powder is designed to dissolve rapidly on contact with the mucus membrane. The powder is conveniently amorphous, any crystals being present therein having an extremely small size.

If desired other nasal pharmaceutical excipients may be present in the nasal pharmaceutical compositions of the invention. The exact choice of other excipients present will depend on a number of factors, including stability and tolerability of the resultant pharmaceutical compositions. Several excipients have been described in the literature, e.g. by H. J. M. van de Donk et al., in First European Congress of Biopharmacy and Pharmacokinetics, 1-3 Apr. 1981, Editors J. M. Aiache and J. Hirtz, Clermont-Ferrand, p. 406-413. For example, an anti-oxidant or conservation agent such as sodium metabisulphate or methyl parahydroxybenzoate or preferably benzalkonium chloride, cetylpyridinium chloride, phenododecinium bromine, sodium benzoate, sodium propionate sodium sorbate, or a protective gas such as carbon dioxide or nitrogen, may be present. The concentration of anti-oxidant or conservation agent in a solution may be for example from 0.001 to 2 percent. If desired a tenside may be present, such as sorbitan monooleate. Naturally the amounts of pharmaceutical excipients are conveniently kept as low as possible, e.g. in a liquid form less than about 5% of the amount of active agent.

When the nasal pharmaceutical composition is in solid form then an inert carrier may be employed, which may represent for example from about 85 to 97.5% of the composition. Alternatively no inert carrier may be necessary.

It is preferred to administer a nasal spray which is isotonic with respect to the ciliary mucus. Conveniently the osmotic pressure of liquid providing the spray is from about 200 to 600 mOsm, especially from 280 to 360 mOsm, per liter. The desired osmotic pressure may be obtained by the addition of any conventional non-toxic isotonizing agent. Sodium chloride may for example be used. Preferably a non-toxic sugar is used, especially glucose.

The exact amount of isotonizing agent to be present depends, inter alia, on the osmotic power of the particular isotonizing agent and the osmotic pressure of the other constituents in the nasal pharmaceutical composition of the invention.

The final pH of the composition of the invention is preferably between about 3.5 and about 9 especially from 3 to 4.

The desired pH may be achieved by means of the presence of a buffer system, e.g. acetic acid/sodium acetate, carbon dioxide (e.g. as a bicarbonate or a hydrogen phosphate or as a protective gas) and a PBS buffer.

The nasal pharmaceutical compositions of the invention may be formulated in conventional manner, e.g. by admixture of the constituents e.g. to form a solution in water, if desired followed by filtering of the solution and/or sterilising under conventional conditions, e.g. by heating. If a powder pharmaceutical composition is desired then preferably a lyophilizate is produced by freeze-drying a chilled solution of the nasal pharmaceutical composition in a vacuum.

The nasal pharmaceutical compositions of the invention in use are conveniently packaged in conventional manner in a nasal spray applicator adapted to produce a spray of the composition. If desired pressure of a compressed gas, e.g. air, nitrogen or ultrasonic means may be used to provide the spray. The applicator may be constructed to receive a unit dosage form, e.g. an ampoule, a capsule or the like containing an appropriate amount of the nasal pharmaceutical composition according to the invention for a unit dose. The ampoule may be of an appropriate volume, e.g. 0.5 to 10 ml to provide several doses of the nasal pharmaceutical composition. Numerous suitable nasal spray applicators are known, e.g. "Microcompack" from Aerosol Services AG, CH-4313 Moehlin, Switzerland, or applicators from Valois S. A., Le Neubourg France, both of which provide liquid sprays.

When the nasal pharmaceutical composition of the invention is liquid then the volume of composition to be dispensed in one dose may vary between wide limits. A suitable volume is from 0.1 to 0.2 ml. Suitable concentrations of active agent are for example from about 0.1 to about 0.45% (i.e. 1 to 4.5 mg/ml) preferably about 4 mg/ml, e.g. 3 to 3.9 mg/ml. The particle size of the spray is preferably greater than 10 microns, e.g. in the range of from about 10 to 1000, e.g. 800 to 1000 microns.

When the nasal pharmaceutical composition of the invention is solid, the volume and particle size of composition to be administered in a single dose may be also vary within wide limits. Suitable concentrations of active agent are from about 0.4 to 10%. Preferably the volume is in the range of about 0.1 ml and the particle size is from about 10 to 1000, e.g. 800 to 1000 microns.

A particularly preferred nasal pharmaceutical composition of the invention contains an aqueous solution of nicardipine.

The nasal pharmaceutical compositions of the present invention are useful for the same indications requiring systemic administration, e.g. cardiac and cerebral disorders, as orally or bucally administered compositions containing the same active agent, e.g. angina pectoris, hypertension, cerebral insufficiency, etc, and particularly for the treatment of acute attacks, e.g. of angina pectoris.

This activity has been confirmed by standard bioavailability trials wherein nasal pharmaceutical compositions of the invention are compared with other conventional compositions and blood levels of drug are measured.

In one trial, a nasal composition of the invention comprising 4 mg nicardipine hydrochloride per ml of distilled water has been administered nasally to rhesus monkeys (weight from 7 to 12 kg). A dose of 0.5 ml of this composition is sprayed each morning into each nostril. Blood samples are taken up 15 minutes, 30 minutes, 1 hour, 2 hours, 3 hours, 4 hours, 6 hours, 8 hours and 24 hours after administration and treated with lithium heparin. The treated blood samples are centrifuged and the concentration of nicardipine in the plasma is determined in conventional manner by converting the nicardipine into a corresponding pyridine derivative and determination by gas chromatographic techniques. The same animals are also treated in another similar trial with orally administered nicardipine at a dose of 20 mg by mean of a gastric tube. The results obtained are as follows:

|  | Oral route (20 mg) | Nasal route (4 mg) |
|---|---|---|
| $C_{max}$ (mg.ml$^{-1}$) | 91.4 ± 11.8 | 101.8 ± 9.3 |
| $T_{max}$ (h) | 2.1 ± 0.5 | 0.4 ± 0.1 |
| AUC 0–24 h (ng/ml$^{-1}$/h) | 457.4 ± 86.6 | 191.5 ± 36.3 |

($C_{max}$ = maximum concentration;
$T_{max}$ = time for to obtain $C_{max}$;
AUC = area under the curve)

As can be seen from the table, bearing in mind that the oral dose was 5 times that of the nasal dose, the bioavailability of nasal route is about 230% that of the oral route. Moreover, the results indicate that calcium antagonists of the invention are rapidly absorbed from the nasal mucus into the systemic blood circulation without a significant first pass effect. The calcium antagonists of the mention are therefore usefully administered nasally.

The exact dosage range for nasal administration of the calcium antagonists according to the present invention will depend on the compound chosen, the condition to be treated, etc. In general the dose to be administered will be such that the same level of concentration of compound in the blood over 24 hours is obtained as for oral administration. The doses are often 2 to 10 times lower than the oral doses. Satisfactory daily doses lie in the range of 5 to 20 mg, conveniently administered if desired 2 to 6 times a day in doses of from about 1 to about 15 mg. For nicardipine, the preferred daily dose is from about 1 to about 6 mg, e.g. containing 0.5 to 6 mg. Preferably the calcium antagonists of the invention are the sole nasal therapy for the condition to be treated.

The following example illustrates the invention:

EXAMPLE

1. Composition

| Constituent | per 1 ml | per 10 litres |
|---|---|---|
| Nicardipine hydrochloride | 0.004 g | 40 g |
| Water to | 1 ml | 10 l |

2. Preparation of the composition 40 g nicardipine hydrochloride are dissolved in 10 liters of water. The mixture is filtered in the presence of carbon dioxide through a filter (0.22 micron holes).

3. Filling of ampoules

Ampoules are filled with a maximum of 1 ml solution under carbon dioxide, sealed and then are sterilized in an autoclave at 121° C. for 5 minutes.

4. Use

The ampoules are broken open and then inserted into a conventional nasal dispenser. The dispenser sprays for each dose about 0.13 ml of solution containing 0.52 mg of nicardipine hydrochloride. The dose is applied into each nostril when required in the treatment of angina pectoris up to 6 times a day.

I claim:

1. A method of treating a host to alleviate cardiac and cerebral disorders which comprises administering to said host through the nasal mucous membrane a pharmaceutical composition containing in single dose form from about 0.5 to about 20 mg. of nicardipine or nicardipine hydrochloride and a pharmaceutically acceptable nasal carrier.

2. The method according to claim 1 wherein the condition is angina pectoris.

3. The method according to claim 1 wherein the condition is hypertension.

4. The method according to claim 1 wherein the condition is cerebral insufficiency.

5. The method according to claim 1 wherein a composition is administered in liquid spray form.

6. The method according to claim 5 wherein the concentration of active agent is from 0.1 to 0.45 percent by weight.

7. The method according to claim 5 wherein the composition is to provide a spray of particles of 10 to 1000 microns.

8. The method according to claim 7 wherein the composition contains sorbitan mono-oleate.

9. The method of claim 1 wherein said carrier is water.

10. The method of claim 1 wherein said carrier is a gas.

* * * * *